(12) United States Patent
Braun et al.

(10) Patent No.: US 6,740,295 B2
(45) Date of Patent: May 25, 2004

(54) METHOD AND DEVICE FOR DETECTING THE TYPE OF REPLACEABLE PISTON-CYLINDER UNITS FOR PIPETTING OR DOSING APPARATUS

(75) Inventors: Ralf Braun, Kreuzwertheim (DE); Peter Mahler, Kreuzwertheim (DE); Jürgen Schraut, Waldbuttelbrunn (DE)

(73) Assignee: Brand GmbH + CO KG, Wertheim (DE)

( * ) Notice: Subject to any disclaimer, the term of this patent is extended or adjusted under 35 U.S.C. 154(b) by 438 days.

(21) Appl. No.: 09/780,678

(22) Filed: Feb. 12, 2001

(65) Prior Publication Data
US 2001/0019701 A1 Sep. 6, 2001

(30) Foreign Application Priority Data
Apr. 1, 1999 (DE) .......................................... 199 15 066

(51) Int. Cl.⁷ .................................................. B01L 3/02
(52) U.S. Cl. ...................... 422/100; 73/864; 73/864.01; 73/864.11; 73/864.16; 73/864.18; 222/287; 222/288; 222/326
(58) Field of Search ............................... 222/287, 288, 222/326

(56) References Cited

U.S. PATENT DOCUMENTS

| | | | | |
|---|---|---|---|---|
| 4,084,730 A | * | 4/1978 | Franke et al. | 73/864.13 |
| 4,779,467 A | * | 10/1988 | Rainin et al. | 73/864.17 |
| 5,389,341 A | | 2/1995 | Tuunanen et al. | |
| 5,620,660 A | * | 4/1997 | Belgardt et al. | 422/100 |
| 5,620,661 A | * | 4/1997 | Sch urbrock | 422/100 |
| 6,019,004 A | * | 2/2000 | Conley et al. | 73/864.16 |
| 6,254,832 B1 | * | 7/2001 | Rainin et al. | 422/100 |
| 6,299,841 B1 | * | 10/2001 | Rainin et al. | 422/100 |
| 6,540,964 B2 | * | 4/2003 | Kohrmann et al. | 422/100 |
| 2002/0177237 A1 | * | 11/2002 | Shvets et al. | 436/180 |

FOREIGN PATENT DOCUMENTS

EP 0 691 158 A2 1/1996

* cited by examiner

Primary Examiner—Jill Warden
Assistant Examiner—Brian R Gordon
(74) Attorney, Agent, or Firm—Nixon Peabody LLP; David S. Safran

(57) ABSTRACT

A method for detecting the type of replaceable piston-cylinder unit mounted in pipetting or dosing apparatus with the help of a code marking on the piston rod head, so as to eliminate the influence of the chain of tolerances piston rod head/piston rod/piston/cylinder bottom/cylinder flange so that, to a certain extent, larger tolerances may be tolerated for the parts of the piston-cylinder units involves generating relative movement between the piston rod head and a detection device, and thereby detecting a reference point on the piston head with the detection device from laterally of the piston head, and generating relative movement between the piston rod head and the detection device and thereby detecting a code marking of the piston rod head in order to determine the type of piston-cylinder unit mounted. Apparatus is provided with which relative movement is produced between the piston rod head and the detection device by a drive device, and during this movement, a reference point on the side of the piston head as well as the code marking are detected by the detection device, and the code marking is evaluated with respect to the reference point. Also, a replaceable piston-cylinder unit for a pipetting or dosing system is provided which has a code marking on the piston rod head by which the type of the piston-cylinder unit is identifiable, the code marking being detectable by a detector positioned laterally of the piston rod head when the the piston-cylinder unit is mounted in a pipetting or dosing apparatus.

21 Claims, 6 Drawing Sheets

METHOD AND DEVICE FOR DETECTING THE TYPE OF REPLACEABLE PISTON-CYLINDER UNITS FOR PIPETTING OR DOSING APPARATUS

BACKGROUND OF THE INVENTION

1. Field of the Invention

The invention relates to a method for detecting the type of replaceable piston-cylinder units for pipetting or dosing apparatus in which a piston of a piston-cylinder unit is connected with a piston rod, on the free end of which a piston rod head is positioned a code marking which may be sampled for determining the type of the inserted piston-cylinder unit, and in which the pipetting or dosing apparatus has a detection device for automatically identifying the piston-cylinder unit the piston-cylinder unit is inserted in the apparatus. The invention relates to a pipetting or dosing system as well as to a replaceable piston-cylinder unit for a pipetting or dosing system of the type used in the performance of such a method.

2. Description of Related Art

A method for detecting the type of a replacement part in the form of a respective piston-cylinder unit mounted on a pipetting apparatus is known from published European Patent Application EP 0 691 158 A2. For implementing the known method, a detection device is designed for identifying the type of the replaceable part with the help of its piston. Here, the piston has a code marking on its piston rod head, and the piston-cylinder unit is inserted into a receptacle of the pipetting device, so that the code marking is placed in a predetermined position relative to the detecting device. If the detecting device is formed, for example, as a photoelectric cell, identification of the type of the replaceable part is then carried out by evaluating the received light passages, or unsuccessful light passages at positions at which the code marking prevents such a passage of light.

This method requires observance of relatively high degrees of accuracy during manufacturing of the parts of the piston-cylinder unit, as the chain of tolerances piston rod head/piston rod/piston/cylinder bottom/cylinder flange is decisive for maintaining the exact relative position between the code marking and the detecting device.

A method for detecting the respective type of replaceable part mounted on a pipetting device in the form of a piston-cylinder unit is also known, wherein the influence of the chain of tolerances piston rod head/piston rod/piston/cylinder bottom/cylinder flange is eliminated. In this method (U.S. Pat. No. 5,389,341), the code marking is not mounted on the piston rod head, but on the cylinder flange. Such a code marking on the cylinder flange has drawbacks as explained in published European Patent Application EP 0 691 158 A2, column 1, line 42 to column 2, line 2.

SUMMARY OF THE INVENTION

The invention is thus based on the problem of designing and developing the known method for detecting the type of replaceable piston-cylinder units for pipetting or dosing apparatuses with the help of the code marking on the piston rod head, so as to eliminate the influence of the chain of tolerances piston rod head/piston rod/piston/cylinder bottom/cylinder flange so that, to a certain extent, larger tolerances may be tolerated for the parts of the piston-cylinder units.

A solution to the problem indicated above is obtained in acccordance with the method of the invention by generating relative movement between the piston rod head and the detection device and thereby detecting a reference point on the side of the piston head with the detection device, and by generating relative movement between the piston rod head and the detection device and thereby detecting a code marking of the piston rod head in order to determine the type of piston-cylinder unit mounted.

A solution to the problem indicated above is obtained in acccordance with the apparatus of the invention by relative movement between the piston rod head and the detection device being generated by means of a drive device, and during this movement, a reference point on the side of the piston head as well as the code marking are detected by means of the detection device, and the code marking is evaluated with respect to the reference point.

The objects of the invention also include providing a replaceable piston-cylinder-unit per se for use in a method according to the invention or in a device according to the invention.

In accordance with the method of the invention, the piston-cylinder unit is first inserted into the apparatus and the cylinder is mounted in the apparatus as usual. The piston rod head is coupled with the apparatus in an appropriate way during the insertion movement or subsequently. Next, detection of the presence of the piston-cylinder unit occurs first in order to be sure that such a unit is actually present in the apparatus. This detection may occur, for example, by actuation of an electric contact during the insertion movement.

According to a possible and advantageous course of the method, a reference point on the side of the piston rod head is detected. For this purpose, the piston rod head is moved past the detection device, which is fixedly positioned in the pipetting or dosing apparatus relative to the apparatus. Or else the detection device is moved past the stationary piston rod head. This detection of a reference point on the side of the piston rod head represents, as it were, a calibration for the subsequent detection of the type of inserted piston-cylinder unit, which makes the method according to the invention, at least to a large extent, independent of the differences in the dimensional tolerances of the parts. So by determining the reference point for each detection of type, it is possible to set an initial point for sampling the code marking of the piston rod head. Starting from the reference point, the detection device on the side of the apparatus is given a target, for example, from which instant of time or from which distance after detecting the reference point the detection of the code marking is to be expected or to be carried out.

In the next step of the method, based on the determined reference point, the code marking of the piston rod head is detected, with which the type of the inserted piston-cylinder unit may be determined. Moreover, a relative movement also occurs between the piston rod head and the detecting device. Because the reference point is detected on the piston rod head directly, it is possible to detect the code marking of the type of inserted piston-cylinder unit, practically regardless of tolerances. The tolerance is determined by dimensioning and tolerance in the manufacture of the piston rod head.

Detection of the reference point and of the type code marking may basically occur in any time sequence, therefore also simultaneously, according to the relative positions taken up by the reference point and the code marking, to how the code marking is formed, and to the applied evaluation method, normally an electronic evaluation method.

According to a more preferred embodiment, in a further step of the method, starting from the determination of the reference point, a marking code is determined in order to ascertain whether a piston-cylinder unit specific to the apparatus is present. Moreover, a relative movement between the piston rod head and the detecting device is also performed. If the code marking specific to the apparatus is detected in this step, then subsequent sampling of the code marking of the piston rod head is allowed to proceed, by means of which the type of inserted piston-cylinder unit is detected.

If, however, upon determining the first code marking, it is realized that a piston-cylinder unit not specific to the apparatus is present, the measurement is aborted and/or a relevant display on the apparatus is initiated, which signals to the user the presence of a piston-cylinder unit which is not specific to the apparatus. Then, for example, the relevant available type may be manually entered into the apparatus.

Otherwise, the piston-cylinder unit is removed from the apparatus and replaced with a piston-cylinder unit specific to the apparatus.

The term "specific to the apparatus" means a piston-cylinder unit which comes from a certain manufacturer and is provided with a code marking which specifies the type, and which is detectable in accordance with the method of the invention.

Detection of the reference point, of the specificity to the apparatus and the code marking of the type may basically occur in any time sequence, and therefore, also simultaneously, as already stated above.

In a more preferred embodiment, the reference point may be detected by placing a thrust element on the side of the apparatus, on the piston rod head, preferably on its free face. Here, the piston may be pushed right down to its stop position in the cylinder with the help of the thrust element, in order to make sure that it is placed over the whole surface on the piston rod head. Dead space is thereby minimized in the piston-cylinder unit.

Preferably, the reference point may be detected by detecting a reference mark on the thrust element. This provides the advantage that the thrust element on the side of the apparatus represents a part which is unalterable at each detection, predeterminable as to its shape and size and, whereon the reference mark may be fixed with accurate positioning.

In a further more preferred embodiment, the sampling of the code marking of the piston rod head is carried out in dependence on the distance of motion of the piston rod head. Hence, for example, the magnitude of the distance covered by the piston rod head may be detected on the side of the apparatus and the code marking may be detected at the positions set earlier, and the type of the inserted piston-cylinder unit may be determined from the results of this detection.

The objects of the invention also include the provision of a pipetting or dosing system with an appropriate detection mechanism. According to an embodiment of the invention, the pipetting system or dosing system comprises a pipetting apparatus or a dosing apparatus which may, basically, be built as either a manually operable apparatus or a motor-driven apparatus.

Preferably, the apparatus is an autonomous, hand-held, motor-driven apparatus, which integrates all of the components in a casing. As usual, the components include a drive, preferably a motor drive, a geared device which transforms the rotational movement of the motor into a longitudinal movement of a piston drive, optionally, control electronics, a power supply and a coupling device for linking the piston of the piston-cylinder unit to the piston drive.

The piston-cylinder unit of the pipetting or dosing system according to the invention is formed as a replaceable part in which a sealed piston is movable for the purpose of sucking in and expelling a liquid to be pipetted or dosed. The piston comprises a piston rod on the free end of which a piston rod head is mounted. The piston rod head bears a code marking which specifies the type of the piston-cylinder unit.

Additionally, the pipetting or dosing system according to the invention comprises a detection device for automatically detecting the type of a piston-cylinder unit mounted on the apparatus.

Furthermore, the pipetting or dosing system comprises a drive device which generates a relative movement between the piston rod head and the detection device, wherein a reference point on the side of the piston head and the code marking are detected during this movement by the detection device. Preferably, the drive device of the piston rod head moves past the detection device. However, the detection device may also be moved while the piston rod head stays still.

Preferably, the drive device produces both the movement of the piston rod head and the relative movement. Alternatively, two drive devices may be provided, in particular, when it is desired to move the detection device for detecting the reference point and the code marking in the apparatus.

Normally, in a pipetting or dosing apparatus, a measuring device is available for determining the relative distance covered between the piston rod head and the detection device, or between the piston rod head and the apparatus. This is also advantageous in the pipetting or dosing system according to the invention, so that the distance for the relative movement may also be detected.

Preferably, a photoelectric cell is provided as a detection device. In the simplest case, the photoelectric cell may comprise an infrared diode as a light source on one side, and an infrared detector facing it on the other side of the apparatus, so that the piston rod head, during its movement relative to the detection device, moves right through between these two elements. This provides the advantage that several code markings may be sampled with a single photoelectric cell. Also, the code marking is not bound to a fixed grid.

However, in order to accelerate the detection process, the detection device may also comprise two or more pairs of photoelectric cells (one photodiode as a light source and one photodetector as a receiver, respectively) placed at a distance from one another along the path of motion of the piston rod head in the apparatus.

Furthermore, the pipetting or dosing apparatus is provided with all the required electronics and all the data processing units which are required for carrying out and evaluating the detection of the type of the mounted piston-cylinder unit.

A replaceable piston-cylinder unit for a pipetting or dosing system according to the invention or for application in a method according to the invention is an independently marketable part.

In the following, the invention will be explained in detail with reference to a drawing illustrating only exemplary embodiments. The description of the exemplary embodiments illustrated in the drawing does not limit the extent of protection, which is defined by the patent claims.

DETAILED DESCRIPTION OF THE INVENTION

Figure 1:
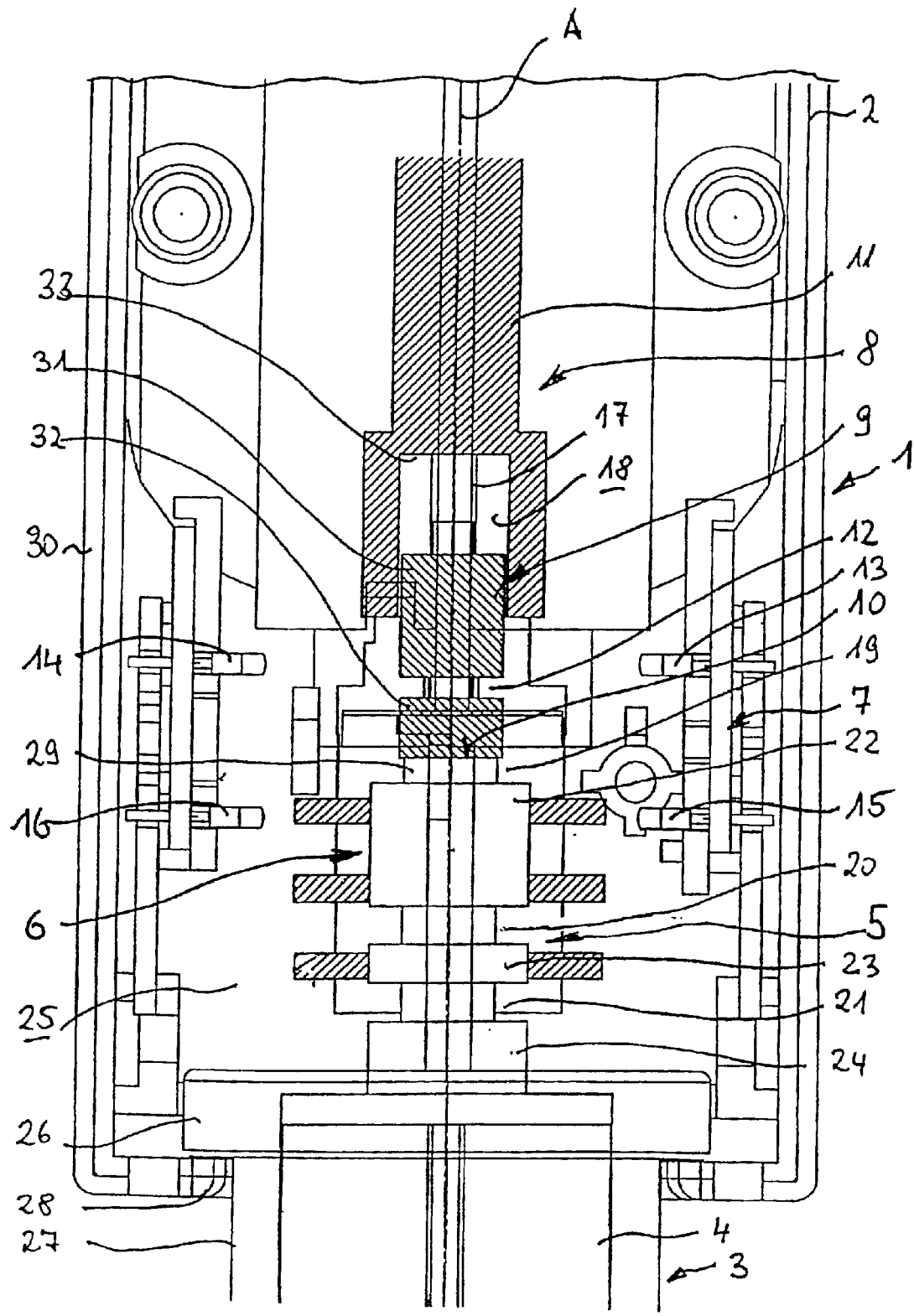
FIG. 1 shows a schematic partial, slightly simplified diagram of a pipetting system according to the invention for explaining the provided components, FIGS. 2–5 each show the pipetting system corresponding to FIG. 1 in a different position of the piston rod head of a mounted piston-cylinder unit for explaining the basics of the method according to the invention.

In FIG. 1, a pipetting system according to the invention 1 is illustrated in part, wherein FIG. 1 is limited to illustrating the components which are required for explaining the present invention. Accordingly, the invention may also relate to a dosing system of a general type.

System 1 comprises a pipetting or dosing apparatus 2, the lower portion of which is illustrated with a receptacle 25 for receiving a piston-cylinder unit 3. All of the other components of apparatus 2, like the manual or motor drive, the geared device for transforming the rotation of the motor into a longitudinal movement for the piston of the piston-cylinder unit, the power supply, the control and evaluation electronics, the controls and the parts of the casing surrounding the latter have been omitted in order to simplify the diagram in FIG. 1.

In the embodiment illustrated in FIG. 1, a partly illustrated piston-cylinder unit 3 is positioned in the receptacle 25. The piston-cylinder unit 3, which may have the shape of a syringe and exist in different sizes, comprises a piston rod 4 at the lower end of which, not visible in FIG. 1, is mounted a piston. The piston and the piston rod 4 are positioned in a cylinder 27, wherein the piston is sealed so that it may perform its sucking and expelling function in the cylinder 27. A piston rod head 5 is provided at the upper end of the piston rod 4, and is provided with a code marking 6 which specifies the type (for example, the size) of the piston-cylinder unit 3.

In the exemplary case, the code marking 6 is formed of a sequence of recesses 19, 20 and 21 which permit the passage of light and of code marking rings 22, 23 and 24. The recesses 19–21 and the code marking rings 22–24 are positioned on the piston rod head 5, so that a recess 19 for the passage of light is first provided at the free end of the piston rod head 5. This recess 19 is used for determining the specific piston-cylinder unit 3 mounted to the respective apparatus. The recess 19 is realized by mounting a projection 29 on the following code marking ring 22, wherein the projection 29 is formed smaller in its diameter dimension as compared with the code marking ring 22 in order to form the recess for the passage of light 19.

After the code marking ring 22, follows the recess 20 for the passage of light, again followed by the code marking ring 23. The third recess 21 for the passage of light is positioned between code marking ring 23 and code marking ring 24.

The piston rod 4, which is positioned in cylinder 27 and able to execute a reciprocating movement, is connected to code marking ring 24.

On the other hand, cylinder 27 comprises a cylinder collar 26, which lies on a suspending grip 28 of a casing 30 of apparatus 2. The cylinder 27 is fixed with the help of a fixing device (not shown), so that only the piston is movable in the cylinder 27 for sucking and expelling liquid.

Apparatus 2 further comprises a detection device 7 for automatically detecting the type of piston-cylinder unit 3 mounted on apparatus 2.

Detection device 7 comprises, in the illustrated embodiment, two infrared photodiodes 13, 15, as light sources, positioned at a distance from one another along axis A of the apparatus, and which preferably are positioned eccentrically with respect to the longitudinal axis of piston rod head 5.

Two infrared photo-detectors 14, 16 are positioned opposite the light sources 13, 15 and at a distance from axis A of the apparatus, as this is shown in detail in FIG. 1.

Apparatus 2 further comprises a drive device 8 which is used here for moving the piston rod head 5 past the detection device 7.

In the illustrated embodiment, the drive device 8 comprises a thrust element 9, which is placed in a guiding space 18 and is movable under elastic preloading of a compression spring 17. The thrust element 9 is similar to a piston and it comprises a guiding section 31 which is positioned in the guiding space 18 and may move into and out of space 18. One end of the compression spring 17 rests on the guiding section 31 and is supported at its other end against the bottom 33 of guiding space 18.

The thrust element 9 further comprises a contact section 32 which is connected to the guiding section 31. A circular ring-shaped recess is positioned between sections 31 and 32 and forms a reference mark 12 for a reference point on the end of the piston head 5 in the illustrated embodiment. This will be explained in more detail hereafter.

The thrust element 9 abuts on a front face 10 of the piston rod head 5 by means of its contact surface 32, which in the exemplary case forms the front face of the projection 29.

In the illustrated embodiment, the drive device 8 is connected with the piston drive so that an extra drive source is not required. The piston rod head 5 is coupled with the drive device 8 in a suitable way, for example, by a snap-on connection, which, however is not shown in detail in order to simplify the illustration in FIG. 1.

FIG. 1 illustrates the state after mounting the piston-cylinder unit 3 on apparatus 2. In this state, through a determination device not shown in detail in FIG. 1, it is only established that a piston-cylinder unit 3 is mounted on apparatus 2. In this state, an identification of whether and the type of piston-cylinder unit is specific to the apparatus has not yet been performed.

Figure 2:
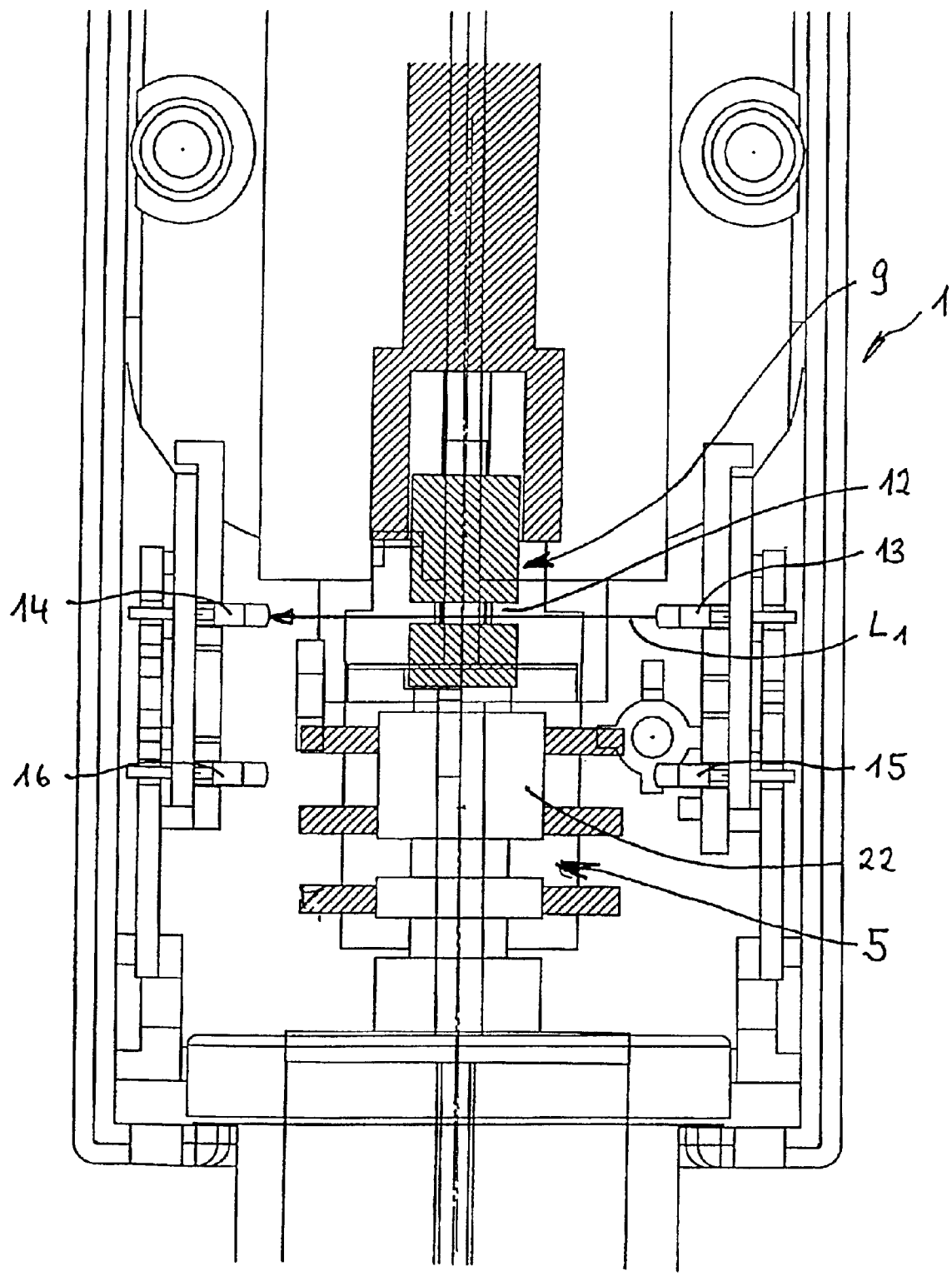

In FIG. 2, the piston rod head 5 has been moved upwards by a certain distance. While performing this movement, the reference mark 12 reaches the area of the light source 13 and first photoelectric cell detector 14. This is indicated by arrow L1. The light source 13 emits the light ray L1 which, because of the form of the reference mark 12, can impinge on the detector 14. This step of the method illustrates the detection of the reference point sideways relative to the piston head. With this step of the method, an initial point is defined, from which the further method steps may be performed following the distance of motion in the illustrated embodiment. Because of the fact that the reference mark 12 is mounted on the thrust element 9 of the apparatus, the dimensional stability of which may be accurately established and which always remains constant, the distance from the reference mark 12 to the front surface 10 is accurately known, as this distance is related to the dimensioning of the contact section 32 of the thrust element 9. After detection of the reference point, the further distance of motion of the piston rod head 5 is determined by a device for measuring the distance of motion (not shown), for example, an indexed disc.

After detection of the reference point according to FIG. 2, the next step in this exemplary embodiment is to detect whether a piston-cylinder unit 3 specific to the apparatus has been mounted on apparatus 2. As noted above, the terminology "specific to the apparatus" means that the piston-cylinder unit 3 used is a device which comes from the manufacturer of the device 2, and that, therefore, in the detection step, which is shown in FIG. 3, a distinction is made between a piston-cylinder unit 3 specific to a given manufacturer and one having nothing to do with that manufacturer.

The piston rod head 5 is moved further upwards, until it reaches the recess 19 for the passage of light in the area of the light source 13 and first photoelectric cell detector 14. The light source 13 emits a light ray L2 which is sensed by detector 14. This means, for the identifier device 7, that a piston-cylinder unit 3 specific to the apparatus is present, so that subsequent detection of the code marking is allowed to proceed for determining the type of this unit. If a piston-cylinder unit 3 having nothing to do with the appropriated manufacturer is present, the projection 29 would not have been provided for forming the recess for the passage of light 19. This would then mean, in the method step according to FIG. 3, that a code marking ring would come and lie in the area between the light source 13 and detector 14, so that the passage of light would be obstructed. This would signal to the apparatus that a piston-cylinder unit 3 having nothing to do with the manufacturer of the device has been mounted, i.e., it is not specific to the apparatus. The consequence would either be a replacement or a display requiring that the type of the piston-cylinder unit 3 be manually entered.

Figure 3:
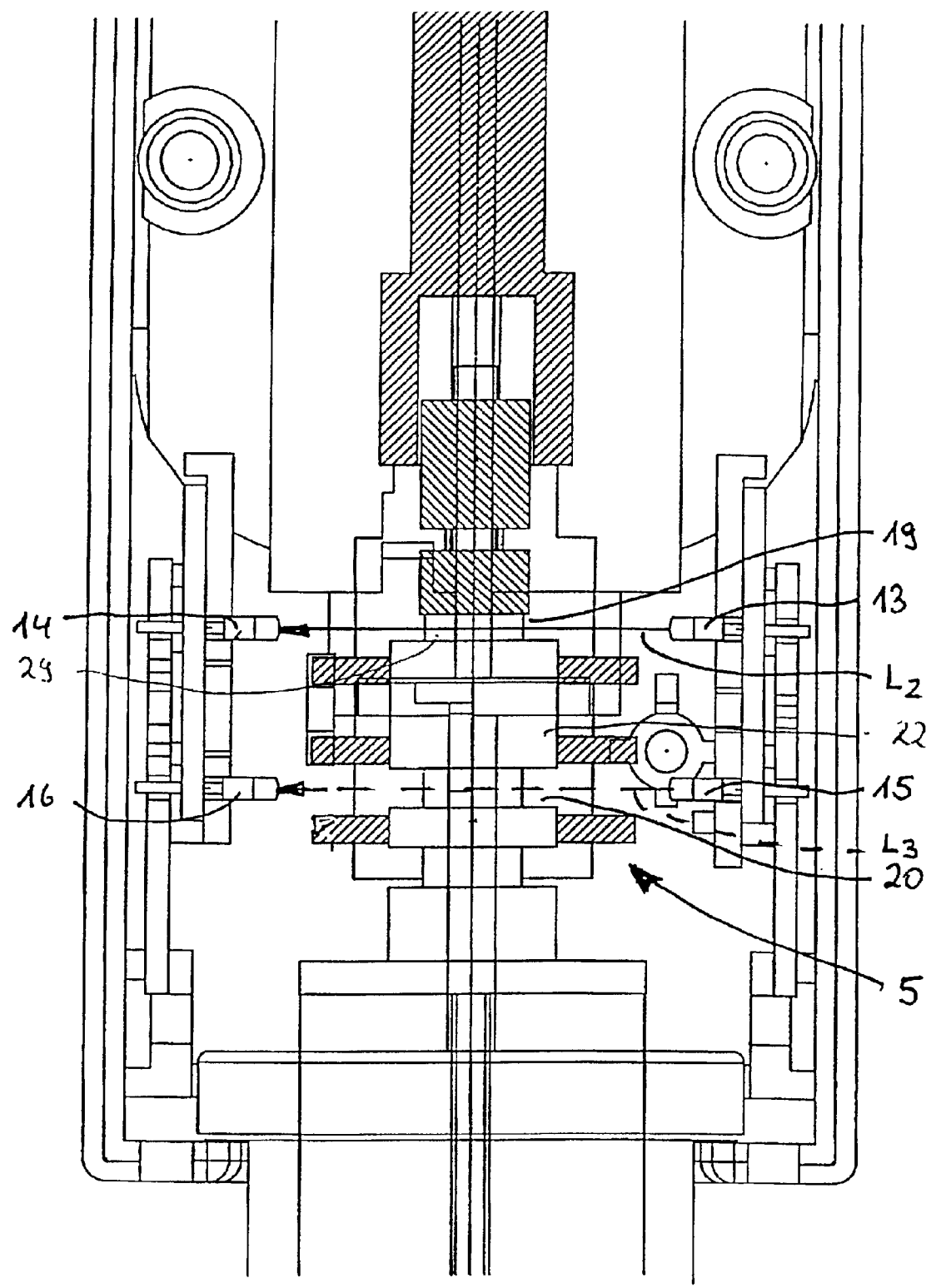

In FIG. 3, in the area of the source 15 and the second photoelectric cell detector 16, a light ray L3 is shown in broken lines. This light ray L3 represents an option, wherein a first sampling of the code marking for detecting the type of piston-cylinder unit 3 is performed simultaneously or slightly offset relative to the step for detecting the appropriateness of the piston-cylinder unit to the specific apparatus. In a simultaneous detection, the result might, for example, be stored in a memory and as soon as it is established that a unit specific to the apparatus has been actually mounted, detection of the type of piston-cylinder unit 3 is allowed to proceed. The advantage of such a simultaneous detection or of a detection just slightly shifted in time is that time is saved in the sampling of the code marking.

Figure 4:
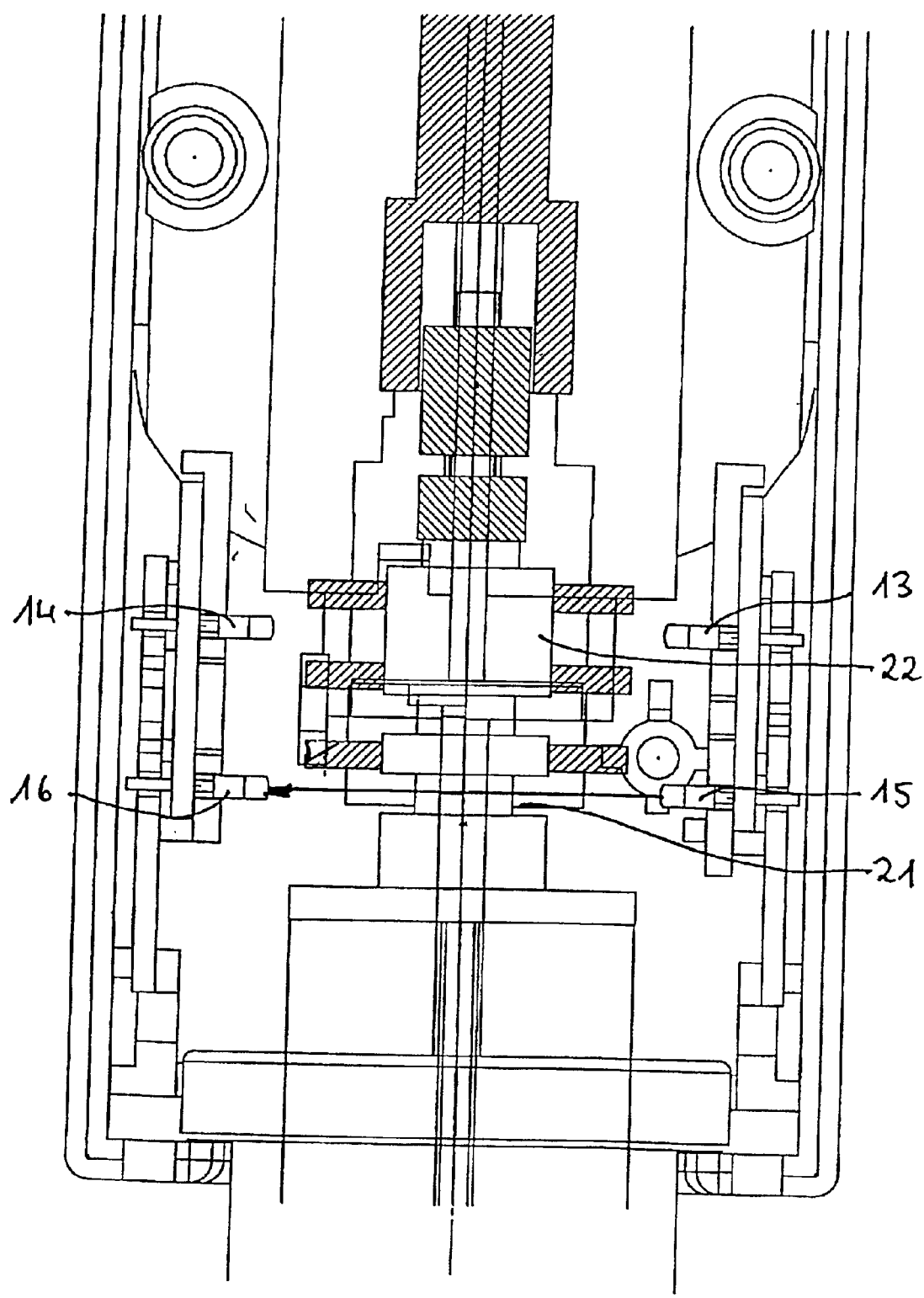

FIG. 4 shows a next step, which is performed with the use of the light source 15 and photoelectric cell detector 16, which samples the recess for the passage of light 21 and transfers the relevant value to an evaluation unit.

Figure 5:
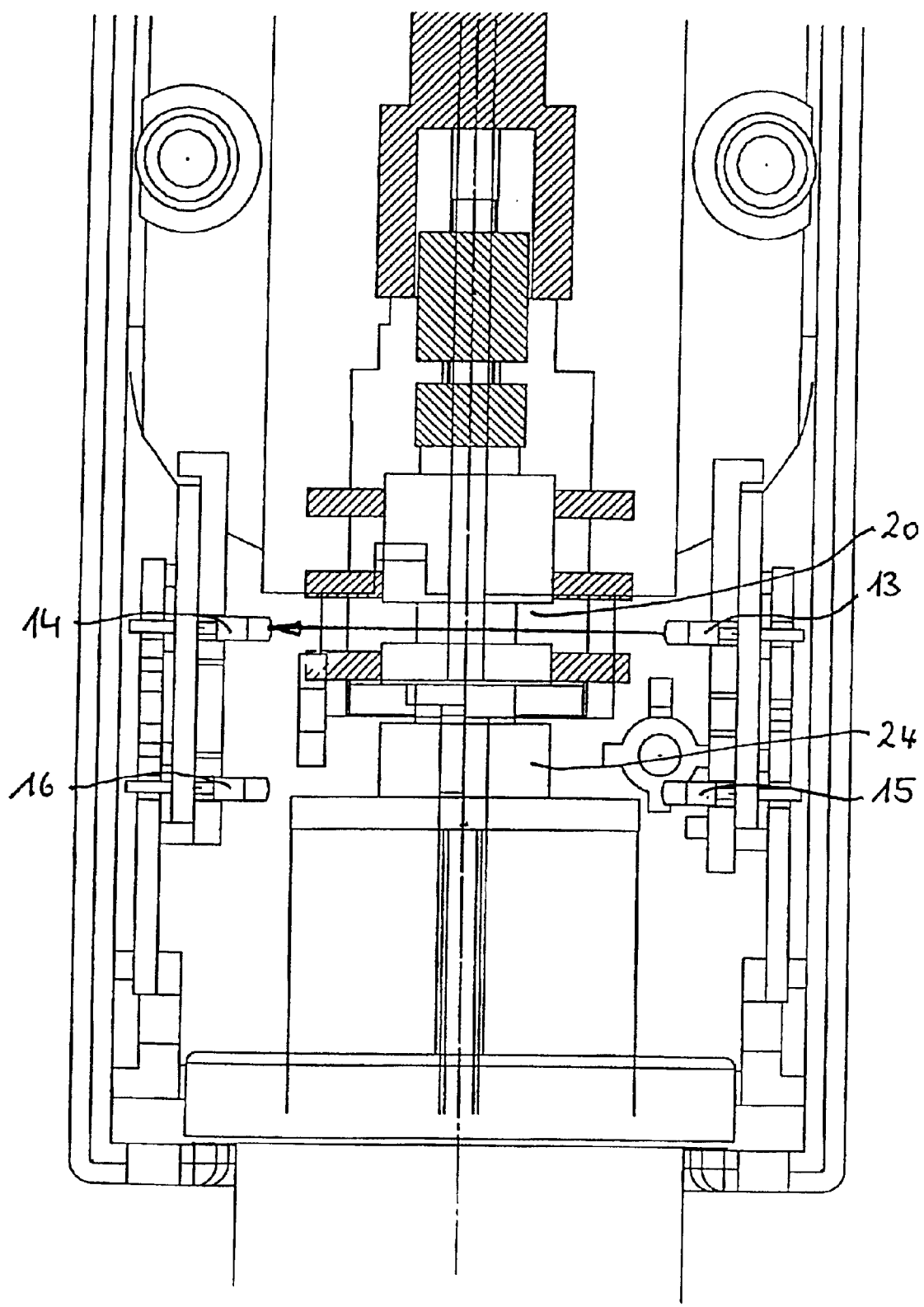

FIG. 5 shows a further detection step for sampling the code marking, wherein the photoelectric cell detector 14 detects the recess 20 for the passage of light from light source 13. This would be an alternative to the procedure according to FIG. 3 when the second photoelectric cell detector 16 is not yet active in the step according to FIG. 3, because it has not yet been established that the piston-cylinder unit 3 is specific to the apparatus.

As it has already been explained, the entire detection or sampling of the code marking is controlled, for example, dependent on distance. This means, that the positions at which the photoelectric cell detectors 15, 16 may expect to find code markings (either recesses for the passage of light from light sources 13, 14, and/or code marking rings), are fixed according to the distance, because the code markings per syringe type are known per se and the dimensional stability of the code marking, even for larger tolerance ranges, is so good, that such pre-programming according to distance is possible in order to sample the code marking with high measurement accuracy.

Figure 6:
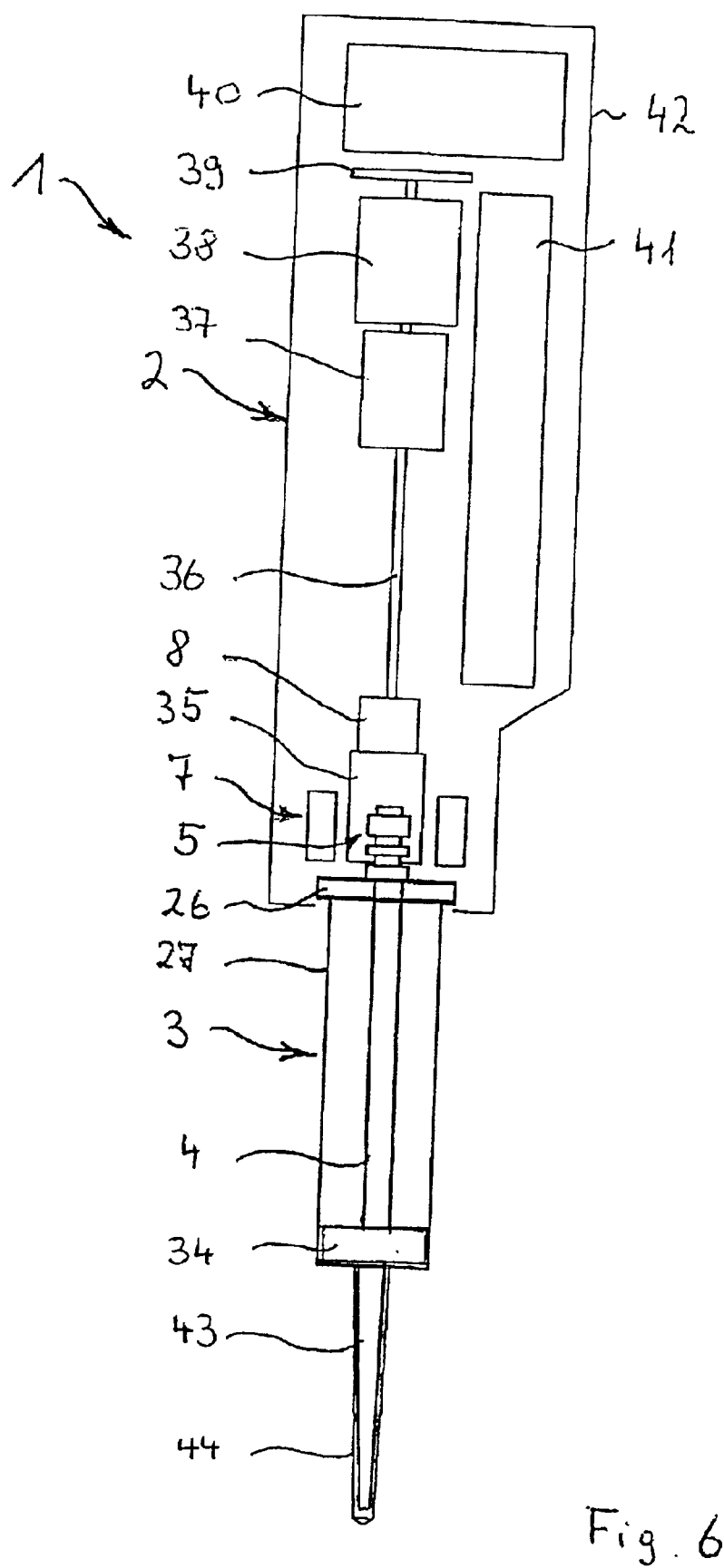
FIG. 6 is a schematic simplified block diagram of a possible embodiment of a pipetting system according to the invention.

In the schematically simplified block diagram of FIG. 6, an example of one possible embodiment of a pipetting system 1 according to the invention is shown. The system 1 comprises an autonomous apparatus 2, which may be held manually, which encloses all of the apparatus components in a casing 42. The apparatus components include, as essential components, control and evaluation electronics 40, in particular for controlling the apparatus and the storage of data. The electronics 40, with the insertion of a distance detection device preferably formed as an indexed disc 39, act together with a drive device 38 that, preferably, is formed as an electric motor and a gearing 37 which operates together with motor 38 to transform rotational movement of the motor into a longitudinal movement of a drive rod 36. In the illustrated embodiment, the drive rod 36 is coupled with the above-described drive device 8, which in turn acts together with a coupling device 35 which fixes the piston rod head 5 to apparatus 2.

The diagram in FIG. 6 further shows the replaceable piston-cylinder unit 3 mounted on apparatus 2 in this operating state, with the piston rod head 5 which is connected to piston rod 4. The piston 34 is positioned on the piston rod 4 at the opposite end of the piston rod head 5, which, in the illustrated embodiment, comprises a piston spike 43, which protrudes into a tip 44 of the piston-cylinder unit 3 at the end position shown in FIG. 6, in order to minimize dead space.

FIG. 6 further clarifies the layout of the detecting device 7, which has already been explained earlier.

What is claimed is:

1. A method for detecting the type of replaceable piston-cylinder unit mounted in a pipetting or dosing apparatus by sampling of a code marking on a free end of a head of a piston rod of the piston-cylinder unit w1114 a detection device of the apparatus, comprising the steps of:

a) inserting the piston-cylinder unit in the apparatus;
   b) mounting the cylinder of the piston-cylinder unit in the apparatus;
   c) coupling the piston rod head with the apparatus;
   d) detecting the presence of the piston-cylinder unit in the apparatus;

and, following the above mentioned sequence of steps comprising the steps of:

e) generating a relative movement between the piston rod head and the detection device and detecting a reference point on the piston head with the detection device; and
   f) generating a relative movement between the piston rod head and the detection device and detecting a code marking on the piston rod head to determine the type of piston-cylinder unit mounted in the apparatus;

wherein the steps e) and f) occur in any time sequence.

2. The method according to claim 1, comprising the further step of:

g) generating a relative movement between the piston rod head and the detection device and detecting a first code marking to determine whether a piston-cylinder unit that is specific to the apparatus is present;

wherein the steps e), f) and g) may occur in any time sequence.

3. The method according to claim 1, wherein the reference point on the piston head is detected by placing a thrust element on a side of the apparatus onto the piston rod head.

4. The method according to claim 3, wherein the reference point is detected by detecting a reference mark on the thrust element.

5. The method according to claim 1, wherein detection of the code marking is carried out in dependence on the distance of said relative motion between the piston rod head and the detection device.

6. The method according to claim 2, wherein detection of the code markings is carried out in dependence on the distance of said relative motion between the piston rod head and the detection device.

7. The method according to claim 1, wherein detection of the code marking is carried out at two or more spaced measurement points on the side of the apparatus.

8. The method according to claim 2, wherein detection of the code markings is carried out at two or more spaced measurement points on the side of the apparatus.

9. A method according to claim 1, wherein the relative movement between the piston rod head and the detection device always is a movement along the longitudinal axis of the piston rod.

10. A pipetting or dosing system, comprising:

a pipetting or dosing apparatus;

a removably mountable piston-cylinder unit formed as a replaceable part, and which comprises a piston with a piston rod and a piston rod head which is provided with a code marking specifying the type of piston-cylinder unit and a reference point detectable from laterally of the piston;

a detection device for automatically detecting the code marking and the reference point of the piston when the piston-cylinder unit is mounted on the apparatus;

a drive device for generating relative movement between the piston rod head and the detection device and operable to enable the reference point and the code marking to be position for detection by the detection device; and an evaluating unit operable to evaluate the code marking with respect to the reference point.

11. The pipetting or dosing system according to claim 10, further comprising a measurement device for determining the relative distance covered between the piston rod head and the detection device.

12. The pipetting or dosing system according to claim 10, wherein the drive device comprises a thrust element that is engageable on a front face of the piston rod head.

13. The pipetting or dosing system according to claim 12, wherein the thrust element is resiliently mounted in a guiding sleeve of the drive device.

14. The pipetting or dosing system according to claim 12, wherein the thrust element has a reference mark which forms the reference point.

15. The pipetting or dosing system according to claim 10, wherein the detection device comprises at least one photoelectric cell detector and light emitter.

16. The pipetting or dosing system according to claim 11, wherein the detection device comprises at least one photoelectric cell detector and light emitter.

17. The pipetting or dosing system according to claim 14, wherein the detection device comprises at least one photoelectric cell detector and light emitter.

18. The pipetting or dosing system according to claim 11, wherein the drive device comprises a thrust element that is engageable on a front face of the piston rod head; wherein the thrust element comprises a reference mark which forms the reference point; and wherein the detection device comprises at least a photoelectric cell and at least one light emitter.

19. The pipetting or dosing system according to claim 10, wherein the drive device for generating said relative movement is a drive device for moving the piston rod head.

20. The pipetting or dosing system according to claim 10, wherein a second drive device is provided for moving the piston rod head.

21. A replaceable piston-cylinder unit for a pipetting or dosing system, comprising:

a cylinder and a piston inside of the cylinder, said piston being provided with a piston rod and a piston rod head;

wherein a code marking is provided on the piston rod head by which the type of the piston-cylinder unit is identifiable, said code marking being detectable by a detector positioned laterally of the piston rod head when the the piston-cylinder unit is mounted in a pipetting or dosing apparatus.

* * * * *